(12) United States Patent
Eitan et al.

(10) Patent No.: US 6,512,235 B1
(45) Date of Patent: Jan. 28, 2003

(54) NANOTUBE-BASED ELECTRON EMISSION DEVICE AND SYSTEMS USING THE SAME

(75) Inventors: Guy Eitan, Menorah (IL); Ory Zik, Tel Aviv (IL); David Rosenblatt, Philadelphia, PA (US)

(73) Assignee: El-Mul Technologies Ltd., Yavne (IL)

( * ) Notice: Subject to any disclaimer, the term of this patent is extended or adjusted under 35 U.S.C. 154(b) by 0 days.

(21) Appl. No.: 09/561,958

(22) Filed: May 1, 2000

(51) Int. Cl.[7] .................................................. H01J 27/00

(52) U.S. Cl. ................................. 250/423 F; 250/398

(58) Field of Search .......................... 250/423 F, 397, 250/398

(56) References Cited

U.S. PATENT DOCUMENTS

| | | | |
|---|---|---|---|
| 5,731,228 A | | 3/1998 | Endo et al. ............... 437/228 |
| 5,773,834 A | * | 6/1998 | Yamamoto et al. ....... 250/423 F |
| 5,773,921 A | | 6/1998 | Keesmann et al. .......... 313/309 |
| 5,872,422 A | | 2/1999 | Xu et al. ..................... 313/311 |
| 5,969,362 A | * | 10/1999 | Kawata et al. ............ 250/423 F |
| 5,973,444 A | | 10/1999 | Xu et al. ..................... 313/309 |
| 6,023,060 A | | 2/2000 | Chang et al. ................ 250/310 |
| 6,097,138 A | * | 8/2000 | Nakamoto .................. 313/309 |
| 6,130,429 A | * | 10/2000 | Ambe et al. ................ 250/397 |
| 2001/0019238 A1 | * | 9/2001 | Dai et al. .................... 313/309 |

FOREIGN PATENT DOCUMENTS

| | | |
|---|---|---|
| EP | 0 913 508 A2 | 5/1999 |
| EP | 0 951 047 | 10/1999 |
| JP | 2000086216 | 3/2000 |
| WO | WO 96/42101 | 12/1996 |
| WO | WO 98/05920 | 2/1998 |
| WO | WO 98/11588 | 3/1998 |

OTHER PUBLICATIONS

Kratschmer, E. et al., "An Electron–Beam Microcolumn with Improved Resolution, Beam Current and Stability", JVS, B13 (6), 2498–2503, Nov.–Dec. (1995).

Saito, Y. et al., "Conical Beams from Open Nanotubes", Nature, vol. 389, 554–555 (Oct. 9, 1997).

Yu, M. et al., "Improved Emission Stability of Carburized HfC (100) and Ultrasharp Tungsten Field Emitters" JVS, B13, (6), 2436–2440 (1995).

Saito, Y. et al., "Field emission from carbon nanobutes and its Application to Cathode Ray Tube Lighting Elements", Surf. Sci. 146, 305–311 (1999).

Wang, Q. et al., "A Nanotube–Based Field–Emission Flat Panel Display", Appl. Phys. Lett., vol., 72, No., 22, 2912–2913, (1998).

Collins, P. et al., "A Simple and Robust Electron Beam Source from Carbon Nanotubes", Appl. Phys. Lett., 69 (13), pp. 1969–1971, (Sep. 1996).

(List continued on next page.)

Primary Examiner—Bruce Anderson
(74) Attorney, Agent, or Firm—Nath & Associates PLLC; Gary M. Nath; Todd L. Juneau

(57) ABSTRACT

A device that produces an electron beam with high optical quality for processing a sample, is presented. The optical quality is manifested by very high brightness and low energy spread. The device includes an electron source device comprising an electrode in the form of a shaped first layer, preferably in the form of a conducting crater carrying at least one nanotube, and an extracting electrode, which is formed with at least one aperture and is insulated from the firs layer. The source can be used in any column that requires such properties. The column according to the invention may be a full size or a miniature electron microscope, a lithography tool, a tool used for direct writing of wafers or a field emission display.

31 Claims, 9 Drawing Sheets

OTHER PUBLICATIONS

Bonard, J. et al., "*Field–Emission–Induced Luminescence from Carbon Nanotubes*", Phys. Rev. Lett., vol. 81, No. 71, 1441–1444, (Aug. 17, 1998).

Heer, W. et al., "*A Carbon Nanotube Field–Emission Electron Source*", Science, vol. 270, 1179–1180, (Nov. 17, 1995).

Fan, S. et al., "*Self–Oriented Regular Arrays of Carbon Nanotubes and Their Field Emission Properties*", Science, vol. 283, 512–514, (Jan. 22, 1999).

Wang, Q. et al., "*Field Emission from Nanotube Bundle Emitters at Low Fields*", Appl. Phys. Lett, 70 (24) 3308–3309, (Jun. 16, 1997).

Ren, Z. et al., "*Synthesis of Large Arrays of Well–Aligned Carbon Nanotubes on Glass*", Science, vol. 282, 1105–1107, (Nov. 6, 1998).

Ren, Z. et al., "*Growth of a Single Freestanding Multiwall Carbon Nanotube on Each Nanonickel Dot*", Appl. Phys. Lett., vol. 75, No. 8 1086–1088 (Aug. 28, 1999).

Chang, T. et al., "*Electron Optical Performnce of a Scanning Tunneling Microscope Controlled fields Emission Microlens System*", JVS, B7, (6) 1855–1861 (Nov.–Dec. 1989).

Rinzler, A. et al., "*Unraveling Nanotubes: Field Emission from an Atomic Wire*", Science, vol. 269, 1550–1553 (Sep. 15, 1995).

Dean, K. "*Field Emission Microscopy of Carbon Nanotube Caps*" Appl. Phys., vol. 85, No. 7, 3832–3836, (Apr. 1, 1999).

\* cited by examiner

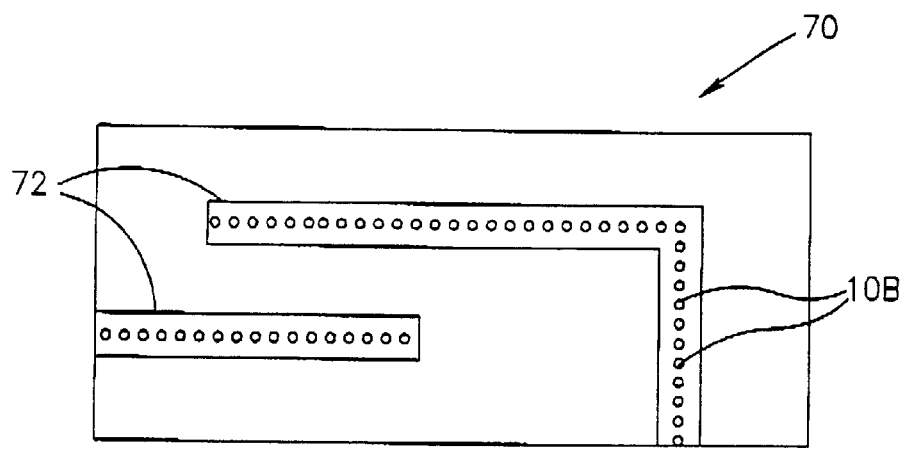
FIG.6A
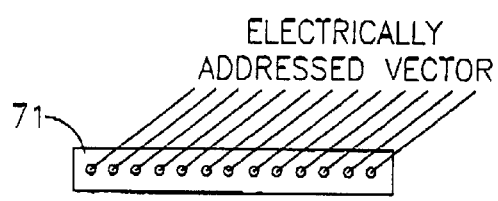
FIG.6B
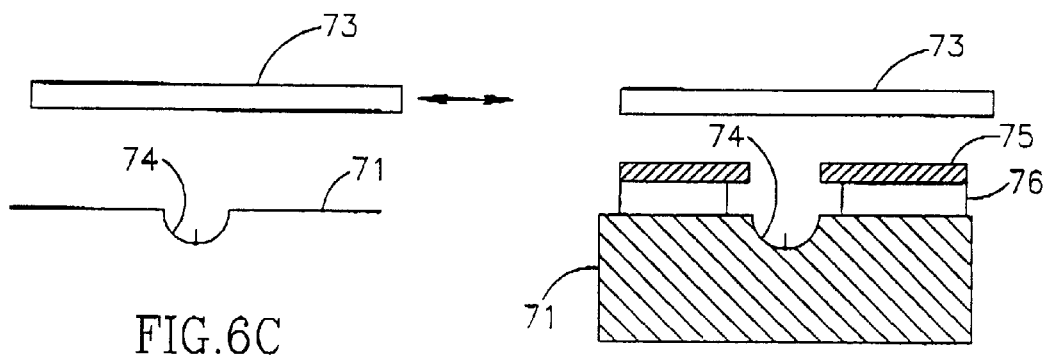
FIG.6C
FIG.6D

NANOTUBE-BASED ELECTRON EMISSION DEVICE AND SYSTEMS USING THE SAME

FIELD OF THE INVENTION

This invention is generally in the field of electron emission based techniques, such as electron microscopy (EM), specifically scanning electron microscopy (SEM), and electron beam lithography (EBL), utilizing a nanotube-based electron emission device, with high electron optical quality, specifically high brightness and low energy spread. The electron emission device of the present invention can be used with any electron beam column or other system that requires such properties.

BACKGROUND OF THE INVENTION

It is the common goal of various applications utilizing an electron beam source, such as SEM and EBL, to have a simple and stable electron beam source, in particular, a source capable of being installed in a miniature device and having high electron optical quality. The simplicity of the electron source is defined by its working conditions, such as operating vacuum and temperature parameters. As for the optical quality, it is predominantly determined by the brightness (i.e., current density per solid angle) and the energy spread of the electron beam. Both the brightness and energy spread determine the amount of current that can be focused on a small spot on the surface of a sample, SEM and EBL are known techniques widely used in various applications, such as the manufacture of semiconductor devices. Electron sources conventionally used in SEM and EBL tools are typically one of three kinds: thermal sources, cold field emitters (CFE), and thermal field emitters or "Schottky-emitters".

An electron beam generated by a thermal source has a wide energy spread, i.e., about 2 eV for tungsten filaments and 1.2 eV for $LaB_6$, and low brightness, i.e., about $10^5$–$10^6$ $A/cm^2 sr$. Consequently, the electron sources of this kind require the complicated construction of an electron beam column, as well as high acceleration voltage, to achieve the resolution of a 1–10 nm.

CFE are characterized by a higher brightness (about $10^8$–$10^9$ $A/cm^2 sr$) and a narrower energy spread (about 0.3–0.4 eV), as compared to that of thermal sources. It is usually made of single crystal tungsten. Such a cathode-electrode requires "flashing" at a high temperature (more than 1800 K) to clean and reform its surface. Moreover, CFE suffer from ultra-high vacuum requirements (e.g., $10^{-9}$–$10^{-10}$ Torr), which is a major factor in the cost of a CFE-based device. Due to the unavoidable adsorption of molecules on the tip-like cathode-electrode, it is complicated to operate CFE in a stable manner.

A TFE source utilizes a compromise concept between those underlying the implementation of the electron sources of the above two kinds. TFE are made of tungsten coated by zirconium oxide, aimed at lowering the work function. These sources, as compared to CFE, are more stable, require lower vacuum (about $10^{-8}$–$10^{-9}$ Torr), and have a comparable high brightness (about $10^7$–$10^8$ $A/cm^2 sr$). A TFE 'source still requires an ultra high vacuum. A further drawback is associated with the need to stabilize the system at a high working temperature, i.e., about 1800° C. The voltage required to achieve a desirable high resolution is typically high. This may damage the sample and/or cause undesirable charging thereof To solve this problem, beam deceleration may be employed. However, this complicates the construction of an electron beam column, and enhances chromatic aberrations. All the conventional electron sources use a very small fraction of the current that is emitted from the electron source. A state of the art Schottty source emits about 100 $\mu A/sr$ with only 10 nA of the source current in a TFE gun can actually be used as a probe current.

As a result of the above disadvantages of the conventional electron sources, their use in EM and EBL tools make these tools expensive and bulky. This impedes their application as integrated tools. Indeed, when using SEM for the inspection of workpieces on a production line, for example, in the manufacture of semiconductor devices, SEM is typically a stand-alone machine accommodated outside the production line. Accordingly, workpieces to be inspected are removed from the production line and brought to the SEM. This slows the production. Moreover, any unnecessary handling of such delicate workpieces as semiconductor wafers is undesirable. Thus, it is highly desirable to use a miniaturized SEM that can be brought to the sample to be inspected, rather than bringing the sample to the SEM. The miniaturized SEM technology is known as "Micro-columns". As for the lithography tools, it is a core challenge of the semiconductor industry, to go beyond optical resolution, which currently limits the minimal feature size of the active elements of a semiconductor device.

Electron beam lithography is not limited by the optical diffraction limit, but by the throughput of the electron beam apparatus. There are three main approaches to this problem. First, the use of a miniature electron beam source device that can be utilized in an arrayed operation ("micro-columns"); second, direct writing in "proximity focus"; and third, the SCALPEL (Scattering with Angular Limitation Projection Electron Beam Lithography). Although these technologies have been known for several years, none of them is used in commercial applications. This is due to the following reasons: the miniaturized arrayed operation is limited by the absence of an adequate electron source, which has the desired electron optical quality (high brightness and low energy spread), which is compatible with miniaturization and with silicon technologies, and which can be produced with sufficient alignment to the optical axis. Currently micro-columns utilize a TFE. The high temperature of the TFE sources places additional limitation on the micro-columns. The proximity focus electron-beam writing was not utilized due to the absence of an electron source that can be patterned in the sub-100 nm scale and that emits electrons with the required electron-optical quality, specifically, a sufficiently narrow angular distribution. The SCALPEL technology is limited by several factors, notably, the small area that can be uniformly exposed by the currently available electron sources.

Attempts have been made to develop electron beam sources with improved electron-optical quality and operating vacuum parameters, so far with no success. Concurrently, carbon-based nanotubes have been developed and studied as field emitters. Their main properties and advantageous features are disclosed, for example, in the following publications:

Shoushan Fan et al., "*Self-Oriented Regular Arrays of Carbon Nanotubes and Their Field Emission Properties*", Science, Vol. 283, p. 512–514, January 1999;

O. H. Wang et al., "*Field Emission from nanotube Bundle Emitters al Low Fields*", Appl. Phys., Lett., 70 (24), pp. 3308–3309, June 1997;

J. M. Bonard et al. "*Field Emission Induced Luminescence from Carbon Nanotubes*" Phys. Rev. Lett., 81, 1441, 1998;

Phillip G. Collins and A. Zetti "A Simple and Robust Electron Beam Source from Carbon Nanotubes", Appl. Phys. Lett., 69 (13), pp. 1969–1971, September 1996;

Walt A. de Heer et al., "A Carbon Nanotube Field Emission Electron Source", Science, Vol. 270, November 1995;

O. G. Wang et al. "A Nanotube-Based Field-Emission Flat Panel Display", Appl. Phys. Lea., Vol. 72, No. 22pp. 2912–2913, 1998;

WO 98/11588; WO 96/42101; EP 0913508; U.S. 5,973, 444; WO 98/05920; and U.S. Pat. No. 5,872,422;

Various molecular morphologies can be grown, known as MWNT (Multi Wall Nano Tubes) and SWNT (Single Wall Nano Tubes). MWNT may be produced as capped or open, and SWNT can appear also as tight bundles. The various nanotubes have been grown with diameters down to a few nanometers.

Although nanotubes are known to have exceptionally good field emission properties (high current at low applied voltage, as well as low energy spread) they did not find their application in EM or EBL. This is largely because the brightness of "bare" carbon nanotubes is essentially low as compared to that of a TFE source. Thus, it is essential to design a gun with superior optical properties that will utilize the elevated field-emission properties of the nanotubes.

According to a technique disclosed in the article of Saito et. al., Nature, vol. 389, $9^{th}$ October 1997, pp 554–5, carbon nanotubes were suspended against an anode plate to obtain a light spot on a fluorescent screen. The source's virtual angular divergence observed was of the same order of magnitude as that of a conventional TFE source, but the total emitted current is lower. This is a strong indication that simply replacing a conventional electron source with a nanotubes-based source does not constitute a satisfactory improvement of the brightness of the source.

As indicated above, the requirement for a miniature electron source is more essential with the development of the micro-column. Prior art techniques of the kind specified disclosed, for example in the articles of Kratchmer et al, JVS, B13, 2498 (1995) and Yu et al, JVS B13, 2436 (1995), and in U.S. Pat. No. 6,023,060, use a "point" electron source which, in principle, emits a diverging laminar electron beam, which is then "cropped" at an aperture (or through a few apertures). These techniques utilized either a CFE or a miniaturized Schottky TFE.

Several publications disclose the emission properties of a single nanotube. The current, I, vs. voltage, V, properties of a single nanotube has been disclosed by Saito et al, App, Surf. Sci. 146,305(1999), Dean et al, J. Appl. Phys. 85, 3832(1999) and Rinzler et al Science, 269,1550(1995). In all these experiments, a few nanometers thick nanotube (of various morphology) was attached to a thin conductor and suspended vertically against an anode plate. In these experiments the distance between the anode and the cathode-tip ranged from about one millimeter to a few centimeters.

In order to compare between the experiments one needs to compare the current vs. the electric field on the tip, the latter being determined by the applied voltage and the experimental setup. If one assumes that the reference electric field is the fixed electric field between two parallel plates separated by a distance, d, which is equal to the distance between the end of a tip and a flat anode plate, then one finds by simple calculation that the electric field on the tip of a very long (to be considered infinite or suspended) and a few nanometers diameter nanotube is enhanced relative to V/d by about two orders of magnitude. In all the above experiments, V/d vs. I may be compared, while taking the field enhancement and the material work function as having the same order of magnitude. One finds that in all the above independent experiments, the current appears at a threshold value of V/d and that the best performing types of nanotubes produce approximately 500 nA at V/d? 0.05 V/$\mu$m. In all cases, a saturation current is obtained. From the results of Saito et al, Nature 389, 554(1997), the angular divergence of the electron beam can also be estimated, as a spot of about 1 cm diameter is seen on a fluorescent screen at a distance of 6 cm. This gives an angular current density of about 40 $\mu$A/sr for a maximum current of 900 nA.

Thus, a single nanotube device can produce a relatively large current for a very low extracting voltage at a distance between a nanotube-tip and anode plate of the order of 1 $\mu$m, but the angular current density will be too small to simply replace the TFE gun utilized within the known designs of micro-columns, U.S. Pat. Nos. 5,773,921 and 5,973,444 and EP0913508 disclose various techniques of micro-fabricating a single nanotube and a plurality of nanotubes on a conducting substrate. In all of these field emission (FE) devices consisting of one or more nanotubes attached to a conducting substrate and separated by an insulating layer, a low voltage extracting gate is utilized. These designs are to be considered "bare", as they simply provide a beam governed by the initial angular divergence. From the angular current density calculated above, it is clear that this device is insufficiently bright as an electron gun for a SEM, EBL or micro-column. As a specific example, if one applies the scaling rules developed by Chang et. al., JVS B7, 1855(1989), to a single nanotube device of this type, it is clear that this device is not appropriate as an electron source in a dual immersion lens electron gun device.

SUMMARY OF THE INTENTION

There is accordingly a need in the art to improve electron source based devices, designed to provide a high brightness and low energy spread, utilizing one or more nanotubes as field emitters.

It is a major feature of the present invention to provide such an electron emission device, which is sufficiently miniature and provides a beam with very high electron optical quality, as required for electron microscopy and other applications. In particular, to improve the brightness of the source the initial angular divergence of the electron beam is to be decreased, as compared to that obtained with the devices of the kind specified disclosed in the above prior art publications.

Generally, the design concept proposed in this invention for reducing the angular divergence of the beam can be applied to other miniature electron sources or macroscopic point sources, and is not limited to nanotubes.

It is a further feature of the present invention to provide such a device, which enables various, important, novel applications of the electron beam source.

A central idea of the present invention is based on the implementation of an electron source with a cathode-electrode which is formed by one or more nanotubes within a specially designed environment, and is associated with one or more gates formed by an anode electrode. According to the technique of the present invention, this is done in a way that minimizes the angular divergence of the beam to the extent that the invention discloses a gun that produces a nearly laminar electron beam. This electron source allows a significant fraction of the current that is emitted from the gun, to be used in a probe. Such an electron source may be used in an electron microscope, either for scanning or transmission purposes, in a lithography tool, in a field emission display and for direct writing purposes.

The nanotube-based electron gun is expected to require lower vacuum conditions (about $10^{-6}$–$10^{-7}$ Torr), as compared to that required by conventional electron sources. The relaxed vacuum requirement is due to the fact that nanotubes are less sensitive to adsorption than conventional emitters. Another reason for the lower vacuum requirement is the "point on a plane" configuration: the nanotubes are situated on a conducting surface, the lines of the electric field are effectively directed between the two planes. Thus, the tendency of ions to be accelerated towards the emitter is significantly decreased.

According to the gun design proposed in the invention, the nanotubes can be assembled in a way that provides very high brightness. The high brightness, combined with the low energy spread (about 0.1 eV), enables a resolution of less than 1 nm to be provided with relatively low accelerating voltages. Since the brightness of the beam, as it exits the electron gun, is high, an optical column attached to the gun can be significantly shorter than the micro-columns known so far. Since heating of the tip-electrode to high temperatures is not required and since the emission drift is small, a carbon nanotube-based bright electron source has obvious advantages.

It is important to note that using one of the nanotubes growing techniques disclosed in the literature (e.g. CVD growth, as disclosed in Shoushan Fan et al., Science, Vol. 283, p. 512–514, 1999 for dense nanotubes, or the technique disclosed in Z. F. Ren., App. Phys. Lett., Vol. 75, p. 1086–1088, 1999 for a single nanotube), the manufacture of such an electron source device can be built in a compatible way to the known silicon processes. The nanotubes are grown self-aligned to an extraction electrode. In a micro-column, they can also be aligned with the other column components. The desired dimensions and optical properties of the gun can be readily determined by charged particle dynamics simulation, which take into account space-charge effects (TRICOMP, by Field Precision, Albuquerque, N. Mex., USA).

Due to the above advantages of the electron source device, its use in a SEM in the manufacture of semiconductor devices will significantly increase the SEM's throughput, due to the shorter pumping time of a sample and due to the fact that the inspection can be done in-situ. It will further increase the throughput due to the ability to provide an arrayed (parallel) operation of a number of columns.

Thus, according to one aspect of the present invention, there is provided a device to be applied to a sample for processing it by an electron beam, the device comprising an electron source device that comprises an electrode in the form of a first conductive layer carrying at least one electrons emitting fiber located inside a crater formed in said first conductive layer for collimating the electron beam produced by the fiber, and an extracting electrode insulated from the first layer, the extracting electrode being formed with at least one aperture located above the crater, the device thereby providing a desired angular divergence of the electron beam.

The term "processing" used herein signifies any treatment that can be applied to a sample by means of an electron beam, such as monitoring, inspection/review, patterning (including mask-making), excitation (e.g., causing the sample's luminescence), etc. The device can be used for an electron microscope (e.g., SEM), a lithography tool, a field emission display, etc. The term "crater" signifies a groove made in the first electrically conductive layer, the electrons emitting fiber projecting from the bottom of the groove. The term "desired angular divergence of the beam" signifies a significantly reduced angular divergence, as compared to that of the prior art devices of the kind specified. The electron-emitting fiber is preferably a nanotube.

The electron source device may be attached to an electron beam column, which can be a miniaturized electron optical system, such as the micro-column. The provision of the electrons emitting fiber inside the electrically conductive crater enables to collimate the emitted beam, thereby significantly increasing the brightness at the exit of the electron source device. Because of the high brightness at the exit of the specified electron gun, the micro-column may be simplified and further miniaturized. For example, it is expected that no further collimation will be required after the gun. Therefore, the device may consist of the gun, the scanner, the detector, and possibly fewer lenses.

The first conductive layer may carry a plurality of electrons emitting fibers (e.g., nanotubes), wherein either several fibers are located in the same conductive crater, or an array of such conductive craters is provided, each for carrying a corresponding one of the fibers.

The ability to control the growth pattern of the nanotubes provides a novel application of the electron source device in a lithography tool for producing the desired features of a semiconductor device on the sample (e.g., wafer), in proximity focus. In other words, the nanotubes are grown on catalysts that are shaped in the form of the desired pattern. The conductive regions, where the catalysts are placed, are built as a two-dimensional cross-section of the conducting crater design disclosed in the current invention, namely, with a specific construction to reduce the angular divergence of the beam.

There is thus provided, according to another aspect of the present invention, an electron microscope to be applied to a sample, the microscope comprising an electron source device and an electron beam column, wherein the electron source device comprises an electrode in the form of a first conductive layer carrying at least one electrons emitting fiber located inside a crater formed in said first conductive layer for collimating the electron beam produced by the fiber, and an extracting electrode insulated from the first layer, the extracting electrode being formed with at least one aperture located above the crater, the device thereby providing a desired angular divergence of the electron beam.

According to yet another aspect of the present invention, there is provided a lithography tool for processing a sample to form its surface with a predetermined pattern, the tool comprising an electron source device having a plurality of electrons emitting fibers producing a plurality of beams each corresponding to one of the pattern features, the beams being spatially separated and aligned in a manner corresponding to the alignment of the pattern features to be obtained on the surface of the sample. The sample itself may serve as an extracting electrode.

More specifically, the present invention utilizes nanotubes as electrons emitting fibers, and is therefore described below with respect to this application.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 6A to 6D illustrate electron source devices according to the invention designed so as to be used in a lithography tool.

DETAILED DESCRIPTION OF A PREFERRED EMBODIMENT

Figure 1:
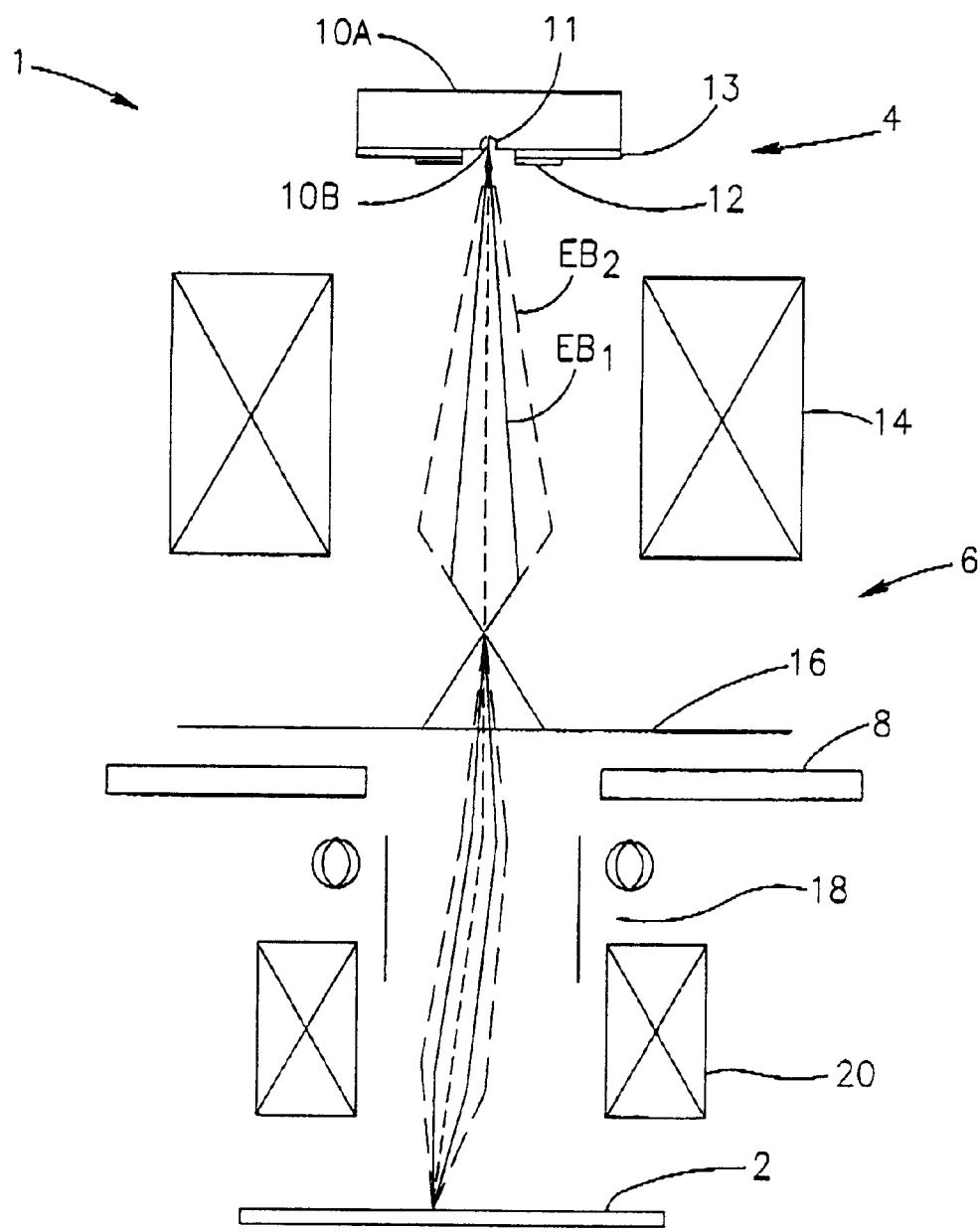
FIG. 1 schematically illustrates a SEM utilizing a high brightness electron emission device according to the invention.

Referring to FIG. 1, there is schematically illustrated a scanning electron microscope, generally designated 1, constructed according to one embodiment of the invention, for inspecting a sample 2 or for processing it with an electron beam. The microscope 1 comprises such main constructional parts as an electron source device 4 and an electron beam column 6 that directs a primary beam towards the sample 2 and directs secondary and back-scattered electrons towards a detector means 8. The latter is appropriately accommodated in the path of electrons knocked out from the sample 2 as a result of its interaction with a primary electron beam.

Figure 2:
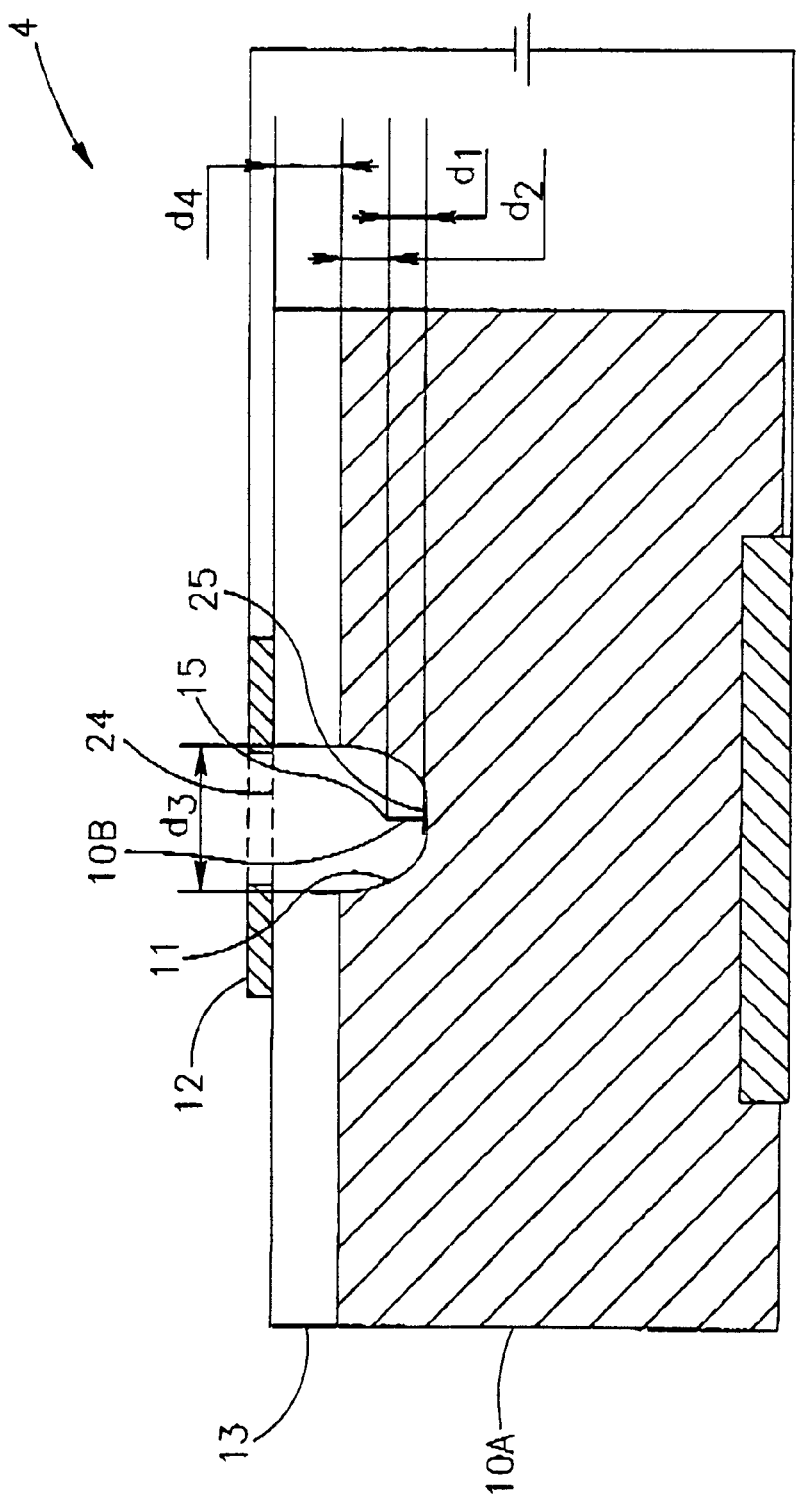
FIG. 2 illustrates more specifically the electron emission device suitable to be used in the SEM of FIG. 1.

As more specifically illustrated in FIG. 2, the electron source device 4 according to the present invention comprises a single nanotube or nanotube bundle 10B located in a crater 11 formed in a conducting layer 10A, and an anode-electrode 12. A nanotube 10B is formed on a metal catalyst 25 on the bottom of the crater 11, such that a tip 15 of the nanotube is located inside the crater 11. The layer 10A and anode-electrode 12 are spaced from each other by an insulating layer 13 with the thickness $d_4$ ranging from 1 $\mu$m to 100 $\mu$m, and are made of suitable electrically conducting materials, such as silicon. Generally, the thickness of the insulator layer 13 is limited by the electrical breakdown conditions.

The nanotubes based gun 4 is fully compatible with silicon processes (e.g. lithography, micromachining and anodic bonding). It is also compatible with any other micromachined or micro-fabricated columns including ceramic-based columns.

To fabricate the device 4 with the silicon-based integrated technology, the insulating layer 13 is deposited onto the substrate silicon layer 10A, and the extractor lens layer 12 is formed on top of the insulating layer 13. Then, the layers 10A, 12 and 13 are patterned so as to form the crater 11 in the substrate layer 10A and to form an aperture 24 above the crater 11. All the layers may and may not be patterned in a single masking procedure. In the example of FIG. 2, the width $d_3$ of the crater 11 is equal to the diameters of the opening made in the layers 12 and 13. In FIG. 1, however, and alternative example is shown, wherein the width of the crater is smaller than the diameter of the opening made in the insulating layer 13. The layer 12 may be a metal electrode for electron extraction. The nanotube 10B is formed on the metal catalyst 25 deposited onto a surface region of the crater. The process of producing a localized nanotube is known (Ren et al, Science 282,1105(1998)).

The nanotube 10B has the length $d_1$, and the tip 15 of the nanotube is spaced a distance $d_2$ from a plane defined by the top of the crater 11 (i.e., from the insulating layer 13). The diameter $d_3$ of the aperture 24 is preferably similar to the diameter of the crater 11. The preferred relationship between these parameters and the thickness $d_4$ of the insulating layer 13 is as follows: $d_1 \approx d_2 \approx d_4 \approx 0.5\ d_3$.

The main conceptual difference between the above design and prior art designs (e.g., U.S. Pat. No. 5,872,422), is that the crater is made in the conductive layer, and such a conductive crater creates a lens structure within the electron gun preventing the divergence of the beam.

Turning back to FIG. 1, the electron beam column 6 is composed of one or more electric and/or magnetic lenses, generally at 14, an aperture 16, a beam deflection system 18, and an objective lens 20. The construction and operation of to the electron beam column are known per se, and therefore need not be specifically described, except to note the following advantageous features of the column 6. Due to the very good emission properties of the nanotube-based electron beam source 4, namely, low energy spread and high brightness as will be described farther below, the number, size and complexity of the column components are significantly is reduced. In particular, almost no apertures are required. Accordingly, a relatively small percentage of the beam needs to be blocked by an aperture 16. That is, the difference between a probe current (i.e., that reaching the sample 2) and emitted current (i.e., that produced by the electron beam source 4) is significantly smaller than in commercial sources. This is schematically illustrated as the figure, showing in solid lines an electron beam envelope $EB_1$ produced by the electron beam source 4 and in dashed lines an electron beam envelope $EB_2$ that is typically produced by the conventional electron source device. The dashed beam envelope schematically illustrates the divergence of the beam as occurs in the prior art without the gun design of the present invention.

Figure 3A:
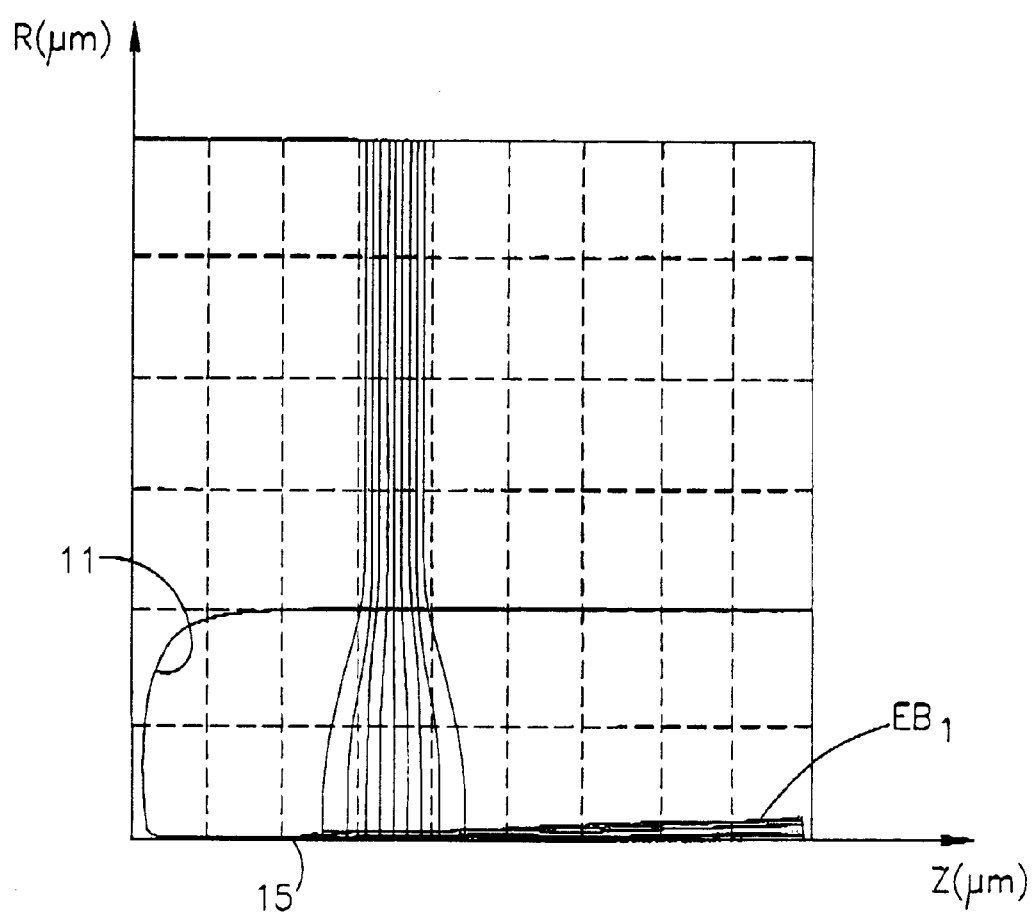
FIGS. 3A–3C graphically illustrate the results of the simulation of operation of the device of FIG. 2 showing improved brightness thereof.
Figure 3B:
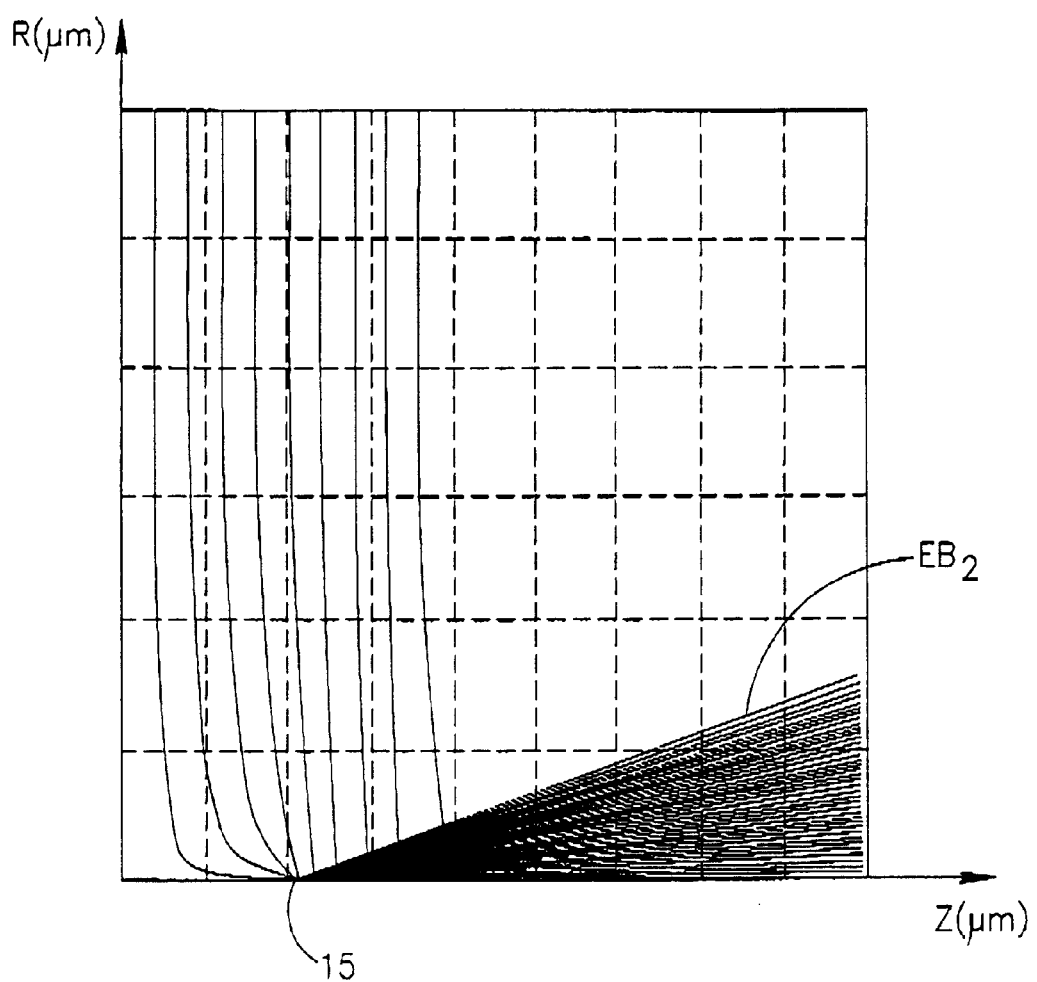
Figure 3C:
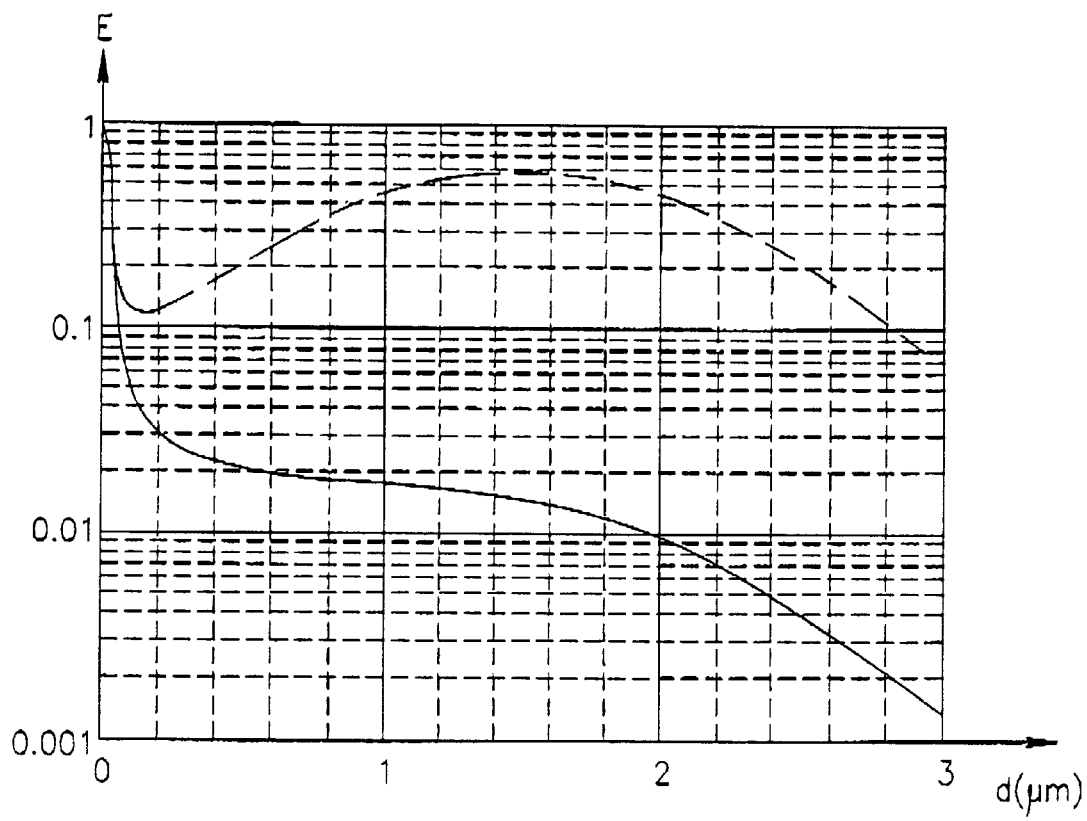

FIGS. 3A–3C illustrate the simulation results. FIG. 3A shows a half cut section of the cylindrical beam $EB_1$, z-axis being the axis of the device, i.e., an axis parallel to the axis of symmetry of the crater 11 (z=0 corresponding to the central bottom region of the crater), and r-axis being directed along the radius of the crater. The emission properties of the nanotube tip are the same as in the prior art (Nature, Vol. 389, $9^{th}$ October 1997, pp 554–555), but the nanotube (of length di) is embedded in the conducting crater, leaving the distance $d_2$ between the tip of the nanotube and the 'edge' of the crater 11. In the simulation, the voltage used to extract the current is 100 V for a 1 $\mu$m insulator gap (thickness $d_4$). As indicated above, this parameter is determined conservatively to withstand the electrical breakdown voltage specifications of the insulator layer. The total current of 500 nA is embedded within a radius 100 nm at a distance of 4 $\mu$m from the gun. In the present example $d_1=d_2=d_4=1\ \mu$m and $d_3=2\ \mu$m. The nanotube length $d_1$ is a tradeoff between the higher voltage that is required when the nanotube is immersed deep in the crater 11 and the collimation of the beam that is lost as the tip of the nanotube is approaching the edge of the crater.

The above dimensions are given as an example only. Generally, the criteria for the determination of these dimensions are as follows:

- the depth of the tip in the crater ($d_2$) affects the amount of the decrease in the field enhancement;
- the diameter of the crater (which is preferably similar to the diameter of the aperture $d_3$), from lens symmetry considerations, affects mainly the amount of field enhancement at the tip.

the thickness of the insulator layer $d_4$ is limited by the electrical breakdown conditions.

FIG. 3B shows a ray-tracing simulation of electrons being emitted from a prior art nanotube device (electron beam $EB_2$), the nanotube tips being identified by the same reference number 15 in FIGS. 3A and 3B to facilitate understanding. This actually presents the divergence of the rays from a gun that does not have such a conducting crater. The total current is again 500 nA. The current in a spot with a 100 nm radius at a distance of 4 $\mu$m from the gun is 75 nA, i.e., 15% of the original current. The overall current is consistent with the experimental values presented by Saito (Nature, Vol. 389, $9^{th}$ October 1997, pp 5545). The extraction voltage used in this figure is 10 V. The field is determined so that the field at the tip in the two configurations shown in FIGS. 3A and 3B is identical.

A comparison of the two configurations is shown in FIG. 3C. The figure plots the total electric field E along the axis of the device vs. the distance along this axis from the nanotube tip 15 to the gate (i.e., extracting electrode 12), normalized to the 'no-crater' tip electric field. The solid line represents a 'no-crater' device (prior art) whereas the dashed line represents the nanotube with a 'crater' device (present invention), with values factorized so that the tip fields are unity for both cases. In order to obtain the same current, this factorization is achievable by varying the voltage. The values of the field are arbitrary and normalized. It is evident that the conducting crater based design accelerates the beam within the gun so that the angular dispersion is diminished. The 'penalty' is the reduction of localized field enhancement by the crater. Consequently, increased voltage has to be used. The reduced angular divergence due to the provision of the crater is evident.

The advantages of the conducting crater based technique may be easily understood from the following tentative argument: The electric field is considerably enhanced on the nano-scale distance, near the nanotube's tip (i.e., local field enhancement). The nano-tip emits with considerable transverse dispersion, which is the main cause for the low brightness. The crater reduces the field amplification, but, being conducting, it creates a parallel beam on a larger scale. A thin carbon nanotube or a thin bundle of a few nanotubes causes large field enhancement which is localized on the 'nano' scale. The crater decreases this field enhancement, so higher applied voltage is needed. Due to the superior field emission properties of nanotubes, this increased voltage is not prohibited by electrical-breakdown conditions. The crater also acts as a lens for the immersed beam. The net result is a beam with decreased angular divergence. A further significant advantage of the crater is the protection of the nanotube or nanotubes from mechanical damage. The nanotubes that are situated in the crater are protected from mechanical damage. It should be noted, although not specifically shown, that the nanotube-based electron beam source device 4 comprises a gun chamber having a vacuum inlet. Due to the use of nanotubes based gun of the present invention, it may be sufficient to have high vacuum ($10^{-6}$–$10^{-8}$ Torr), rather than ultra high vacuum ($10^{-8}$–$10^{-9}$ Torr) in the gun chamber, in contrast to conventional field-emission SEM systems. The high vacuum ensures a sufficient electron mean-free path as well as stability of the electron gun. The crater also protects the nanotube from "poor" vacuum conditions. The crater-based design suppresses possible side emission along the length of the nanotube.

Additionally, one advantageous feature of the SEM 1 (FIG. 1), as compared to the conventional SEM (for example, that commercially available from FEI Inc.), is the reduced chromatic aberrations, due to the reduced energy spread of the electron beam produced by the nanotube-based electron source device 4. The small energy spread is due to the resonant-tunneling process (two-level emission system) of electron emission from nanotubes.

Another advantage is the reduced spherical aberrations that result from the reduced angular divergence of the beam at the gun exit.

It should be noted that, although the above description relates to a SEM, the is electron beam source device 4 could be utilized in an EBL as well as in other tools that utilize an electron beam. The electron beam source device according to the invention can be utilized in small-scale devices, such as a miniaturized SEM (micro-column), which can be used in various fields.

The miniaturization of SEM and other E-beam tools has unique advantages. A miniature SEM can be brought to the sample instead of bringing the sample to a standard SEM. In other words, the miniature SEM can be used as an integrated tool, rather than being a stand-alone machine. As indicated above, electron microscopy systems are used extensively in the semiconductors industry. The present invention will allow a low voltage, high resolution SEM, that will do the desired tasks in-situ.

The quality of the nanotubes based electron source that is proposed in the present invention, and the compatibility with silicon technology, makes it an optimal electron source for miniaturization. Micro-columns are miniature SEMs, typically constructed from layers of silicon or silicon and Pyrex. A micro-column contains most of the components of an electron beam column (apertures, lenses, scanner and detector). The factor that so far impeded the development and commercialization of His device is the absence of a sufficiently bright electron source that will have one or more of the following properties: compatibility with silicon technologies; and stability without resorting to heating.

Figure 4A:
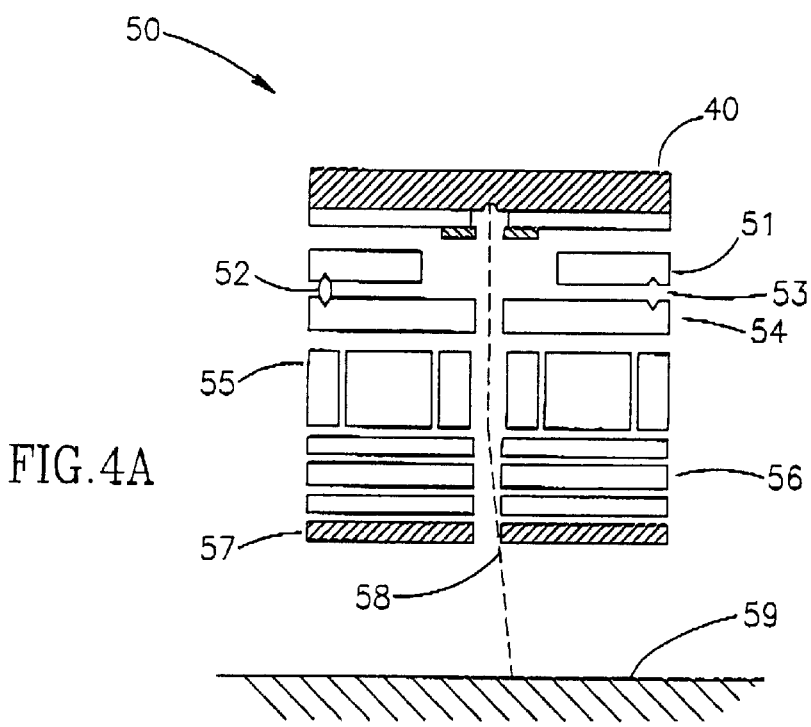
FIGS. 4A and 4B schematically illustrate how the device of FIG. 2 is used with a micro-column.

FIG. 4A illustrates the integration of the nanotube-based source device according to the invention into a micro-column 50. The typical column components that follow the electron beam source device 4 are a spacer 51, that can be aligned with an optical fiber 52 positioned in grooves 53, an aperture 54, a scanner 55, an electrostatic (Finzel) lens 56 and a detector 57. The beam 58 is led through these components to the sample 59. The elevated optical quality of the source 4, may lead to a reduction in the number of column components in the micro-column 50.

Figure 4B:
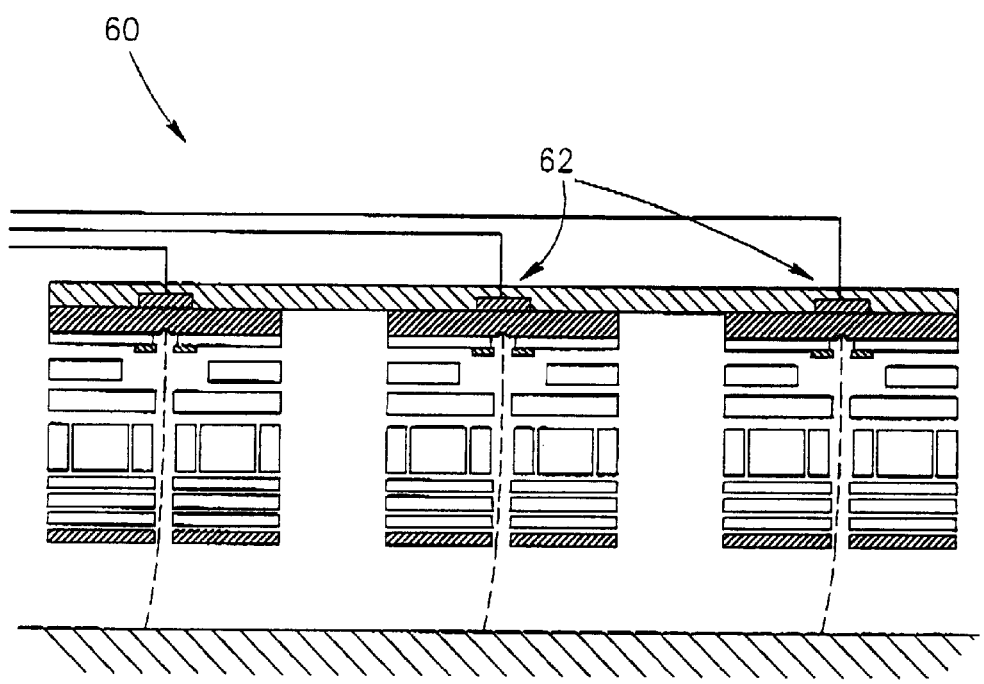

It is important to note that the miniaturization of the electron source device also allows the possibility of arrayed operation on a commensurate scale with present and future semiconductor chip-size. This concept is illustrated in FIG. 4B. It shows a multiple-column structure 60 formed by an array of parallel identical nanotube-based micro-columns, generally at 62, which can be separately addressed electrically, as illustrated in the figure in a self-explanatory manner. Obviously, a two-dimensional array (or matrix) of such micro-columns can be assembled together.

It should be understood that the use of such an array of N micro-columns in an EBL tool would significantly improve its throughput. The arrayed operation will have better performance than high-resolution optical steppers. The multiple-column structure may also be used for multiple-beam inspection, metrology and direct writing techniques.

Figure 5A:
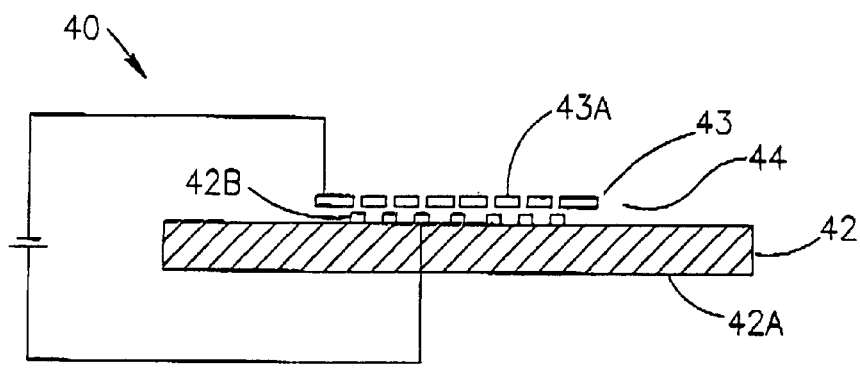
FIGS. 5A to 5C illustrate some more features of the present invention.
Figure 5B:
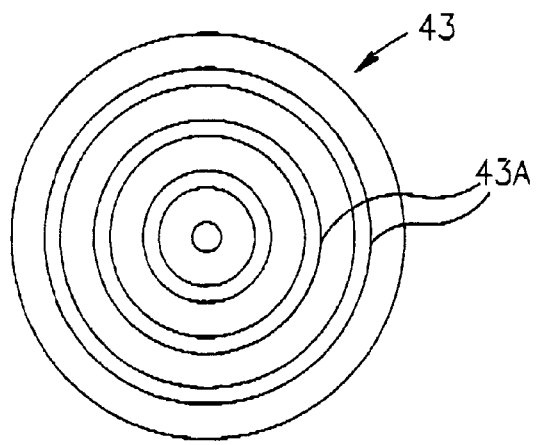

The cathode-electrode may carry an array of nanotubes, wherein either a raw of spaced-apart nanotubes is located in a common elongated crater, or an array of craters is formed in the conducting substrate each carrying a corresponding one of the nanotubes. FIGS. 5A and 5B illustrate front and top views, respectively, of an electron source device 40 composed of a cathode-electrode 42 and an anode-electrode 43 spaced from each other by an insulating layer 44 (e.g., vacuum).

Figure 5C:
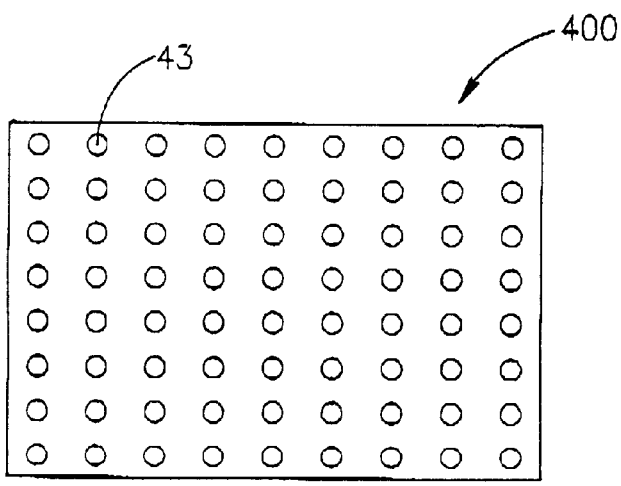

The cathode-electrode 42 includes a substrate 42A (e.g., silicon) carrying an array 42B of nanotubes in crater(s) (which are not specifically shown). An extractor lens 43 is formed as a plurality of spaced-apart apertures 43A in the anode-electrode. As is better seen in FIG. 5I, the extractor lens 43 is in the form of several concentric rings—three rings in the present example, the rings sections serving as apertures, generally at 43A. The rings-based design of the mask may be replaced by any other concentric polygon-structure (e.g., rectangular). FIG. 5C illustrates a matrix 400, composed of elements 43, which is suitable for use in the electron gun 40.

Referring to FIGS. 6A to 6C, there is illustrated an electron source device 70 designed to be used as part of a lithography tool. In the electron source device 70 shown in FIG. 6A, effective (emitting) nanotube-containing regions 72 are shaped and distributed within a substrate layer (e.g., silicon), in accordance with a pattern to be produced on a sample (e.g., semiconductor wafer) by the lithography tool. In other words, each of the regions presents a specific feature of the pattern, and the spaces between these regions correspond to those between the pattern features. Each line of the region 72 is shaped in the form of a conducting elongated crater to create parallel beams. The lines can be fabricated using electron beam lithography techniques to create the pattern of catalyst nanoparticles on which the nanotubes are grown. According to an alternative embodiment of the invention, shown in FIG. 6B, a substrate layer (cathode electrode) 71 is uniformly covered with nanotubes in craters, and each nanotube or group of nanotubes is addressed electrically. As shown in FIG. 6C, a wafer 73 to be patterned may be placed in front of the nanotubes containing region or located on a stage or stepper (not shown), and the pattern is created by moving the wafer with respect to the layer 71.

In a preferred embodiment of the invention, the nanotubes will grow in conducting "elongated craters" or grooves 74, as shown in FIG. 6C. The grooves 74 may be created by standard etching techniques. They are used for collimating the electron beams, as exemplified in the crater-based design. The extractor electrode will be the wafer 73 itself that will be placed in "proximity focus" to the emitting surface. The average nanotubes diameter can be a few nanometers, and the average distance between nanotubes can be the same. According to the example of FIG. 6D, a modification to assist in extracting the electrons, instead of biasing the wafer, can be an elongated gate illustrated by layers 75 and 76. But in principle the voltage can be applied to the wafer to be patterned.

Figure 6E:
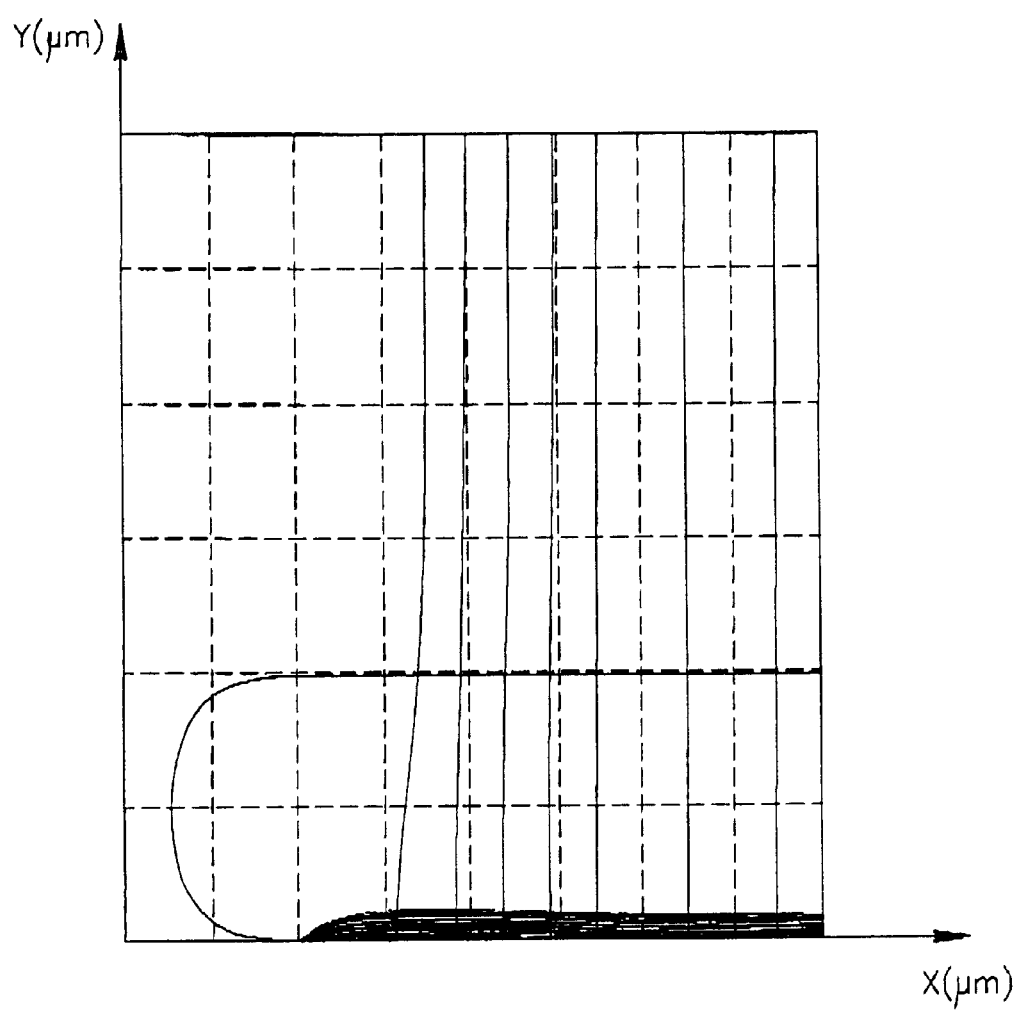
FIG. 6E illustrates the results of a computer simulation of the operation of the lithography tool of FIGS. 6A–6D.

As shown by the simulation results presented in FIG. 6E, the beam in a distance x of 5 μm from the crater is smaller than 100 nm in diameter. The parameters x and y are used to highlight the fact that figure shows a two dimensional cross-section of an elongated crater. The current available in a 100 nm spot from the crater design is up to 500 nA, which is more than required for writing on a resist This current density is available at a working distance of 5 μm from the gun. Larger working distances are also possible.

Since the electron source device that is based on fiber(s), e.g., nanotube(s), in a conducting crater emits with sufficient brightness to be used in electron microscopy, it is evident that a matrix of craters is suitable for a field emission display, where each beamlet correspond to a pixel. Thus, the current invention is also suitable for flat panel displays.

The advantages of the present invention are thus self-evident The electron source device according to the invention enables to solve various constructional and operational problems of electron source device based systems, such as electron microscopes, lithography tools and flat displays. Due to the small size of the nanotube-based electron source device and relaxed vacuum requirements, the entire system can have a desirably small footprint, and can allow for assembling a multiple-column arrangement to be advantageously used in various applications. Due to the elevated optical performance of the electron gun and reduced chromatic and spherical aberrations of the associated electron beam, the performance of the system is significantly improved. In fact, the invention allows to the useful utilization of nanotubes in an electron gun. The use of "patterned" cathode-electrode, and preferably by means of the same anode-electrode, the construction and operation of a lithography tool utilizing such an electron source device is significantly improved.

Those skilled in the art will readily appreciate that various modifications and changes can be applied to the preferred embodiments of the invention as hereinbefore exemplified without departing from its scope defined in and by the appended claims.

What is claimed is:

1. A device for generating at least one electron beam, the device comprising an electron source device that comprises an electrode in the form of a first conductive layer formed with a crater carrying at least one electrons' emitting fiber located inside the crater such that a tip of the fiber is located inside the crater and spaced a certain distance from a plane defined by the top of the crater; and an extracting electrode insulated from the first layer and formed with at least one aperture located above the crater, the device thereby providing collimation of the electron beam produced by the fiber and a desired angular divergence of the electron beam.

2. The device according to claim 1, wherein said at least one electrons emitting fiber is nanotube.

3. The device according to claim 1, wherein said at least one fiber is grown on a catalyst formed on the surface of the crater.

4. The device according to claim 3, wherein said extracting electrode formed with at least one aperture is used as a mask for depositing catalyst therethrough.

5. The device according to claim 1, wherein the extracting electrode is in the form of a second layer spaced from the first layer by an insulating material, formed in an aligned manner.

6. The device according to claim 1, wherein said processing includes at least one of monitoring, inspection/review, patterning, mask-making or excitation technique.

7. The device according to claim 1, wherein for given dimensions of the fiber, a diameter of said at least one aperture, said distance between the fiber tip and the plane defined by the top plane of the crater, and a width of the crater are selected so as to provide maximal optical performance and high emitted current.

8. The device according to claim 1, wherein for given fiber dimensions, the following parameters are approximately identical: a diameter of said at least one aperture; the distance between the fiber tip and the plane defined by the top of the crater; and a width of the crater.

9. The device according to claim 1, also comprising an electron beam column for directing said at least one electron beam towards the sample, wherein the electron beam column a micro-column produced by an integrated technology.

10. The device according to claim 9, wherein said electron source device is integrated into the micro-column by anodic bonding.

11. The device according to claim 1, wherein the first layer electrode carries a plurality of fibers, and the extracting electrode is formed with a plurality of spaced-apart apertures.

12. The device according to claim 11, wherein said plurality of spaced-apart apertures creates a plurality of gates each associated with a fiber-containing region therebelow.

13. The device according to claim 11, wherein said spaced-apart apertures are formed as sections of a plurality of spaced-apart concentric polygons.

14. The device according to claim 11, wherein said plurality of apertures may be in the form of a desired pattern to be produced on the surface of the sample, said device serving as a lithography tool.

15. The device according to claim 11, wherein said plurality of apertures presents a mask through which the plurality of fibers are grown on the first layer.

16. The device according to claim 11, wherein the second conductive layer is in form of a pattern having spaced-apart apertured conductive regions, each conductive region being separately operated by a power source, thereby serving as a separate gate for the corresponding at least one fiber located on the first layer below this conductive region.

17. The device according to claim 16, functioning as a display, each apertured conductive region together with said corresponding at least one fiber presenting a pixel of the display.

18. The device according to claim 1, and also comprising a plurality of the electron source devices each associated with a corresponding one of a plurality of electron beam columns, which assembled together for producing a corresponding plurality of electron beams.

19. The device according to claim 18, wherein each of the electron beam columns is a micro-column.

20. A device to be applied to a sample for processing it by electron beams, the device comprising an electron source device that comprises an electrode in the form of a first conductive layer formed with craters carrying a plurality of electrons' emitting fibers located inside the craters for collimating the electron beam produced by the fiber, and an extracting electrode insulated from the first layer, the extracting electrode being formed with a plurality of spaced-apart apertures formed as sections of a plurality of spaced-apart concentric rings located above the craters, the device thereby providing desired angular divergence of the electron beams.

21. An electron microscope to be applied to a sample, the microscope comprising an electron source device and an electron beam column, wherein the electron source device comprises an electrode in the form of a first conductive layer formed with a crater carrying an electrons' emitting fiber located inside the crater such that a tip of the fiber is located inside the crater and spaced a certain distance from a plane defined by the top of the crater; and an extracting electrode insulated from the first layer and formed with an aperture located above the crater, the device thereby providing collimation of the electron beam produced by the fiber and a desired angular divergence of the electron beam.

22. The electron microscope according to claim 21, wherein said electrons' emitting fiber extends along a central axis of the crater.

23. A lithography tool for processing a sample to form its surface with a predetermined pattern, the tool comprising an electron source device having a plurality of electrons' emitting fibers producing a plurality of beams each corresponding to one of the pattern features, the beams being spatially separated and aligned in a manner corresponding to the alignment of the pattern features to be obtained on the surface of the sample, the electrons' emitting fibers being located inside craters formed in a conductive layer, such that that a tip of the fiber is located inside the crater and spaced a certain distance from a plane defined by the top of the crater.

24. The lithography tool according to claim 23, wherein the sample insulated from said conductive layer serves as an extracting electrode and is placed in proximity focus to an emitting surface defined by the fibers' tips.

25. The lithography tool according to claim 23, wherein each of the electrons' emitting fibers extends along a central axis of the respective one of the craters.

26. A lithography tool to be applied to a sample to produce a predetermined pattern on the surface of the sample, the lithography tool comprising an electron source device and an electron beam column, wherein the electron source device comprises an electrode in the form of a first conductive layer formed with a crater carrying an electrons' emitting fiber located inside the crater such that a tip of the fiber is located inside the crater and spaced a certain distance from a plane defined by the top of the crater; and an extracting electrode insulated from the first layer and formed with an aperture located above the crater, the device thereby providing collimation of the electron beam produced by the fiber and a desired angular divergence of the electron beam.

27. The lithography tool according to claim 26, wherein said first layer carries a plurality of fibers located in the craters arranged in accordance with a predetermined pattern to be produced on the surface of the sample.

28. The lithography tool according to claim 27, wherein said extracting electrode is formed with a plurality of spaced-apart apertures each aperture located above a corresponding one of the craters.

29. The lithography tool according to claim 26, wherein said first layer is uniformly covered with a plurality of spaced-apart fibers, each fiber being addressed electrically; and the sample to be patterned is supported below the first layer for movement relative to the first layer.

30. The lithography tool according to claim 26, wherein said fiber extends along the central axis of the crater.

31. A device for generating an electron beam, the device comprising an electron source device that comprises an electrode in the form of a first conductive layer formed with a crater carrying an electrons' emitting fiber located inside the crater such that the fiber extends along a central axis of the crater and a tip of the fiber is located inside the crater and spaced a certain distance from a plane defined by the top of the crater; and an extracting electrode insulated from the first layer and formed with an aperture located above the crater, the device thereby providing collimation of the electron beam produced by the fiber and a desired angular divergence of the electron beam.

* * * * *